United States Patent
Ishii et al.

(10) Patent No.: US 7,145,163 B2
(45) Date of Patent: *Dec. 5, 2006

(54) APPARATUS FOR DETECTING LIGHT-TRANSMISSIVE SHEET-LIKE BODY

(75) Inventors: Yoshiyuki Ishii, Fujinomiya (JP); Kazuo Onishi, Fujinomiya (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/199,194

(22) Filed: Aug. 9, 2005

(65) Prior Publication Data

US 2005/0269531 A1 Dec. 8, 2005

Related U.S. Application Data

(63) Continuation of application No. 10/060,148, filed on Feb. 1, 2002, now Pat. No. 6,943,363.

(30) Foreign Application Priority Data

Feb. 2, 2001 (JP) .............................. 2001-027150

(51) Int. Cl.
*G01N 21/86* (2006.01)
*G01V 8/00* (2006.01)

(52) U.S. Cl. ........................... 250/559.36; 250/559.39; 356/429

(58) Field of Classification Search ........... 250/559.01, 250/559.04, 559.05, 559.07, 559.08, 559.12, 250/559.19, 559.4, 559.36, 559.26, 559.28, 250/559.29; 399/45, 190, 370, 371, 376; 356/429, 615; 347/19

See application file for complete search history.

(56) References Cited

U.S. PATENT DOCUMENTS

| | | | |
|---|---|---|---|
| 3,594,087 A | 7/1971 | Miranda | 356/444 |
| 4,511,246 A | 4/1985 | Nishiyama | 355/75 |
| 4,713,550 A | 12/1987 | Anzai | 250/559.2 |
| 5,006,719 A * | 4/1991 | Blaser | 250/559.36 |
| 5,260,564 A | 11/1993 | Bruggeling | 250/223 R |
| 5,764,367 A | 6/1998 | Schaede | 356/429 |
| 6,151,117 A | 11/2000 | Tuhro | 356/615 |
| 6,323,948 B1 * | 11/2001 | Haque et al. | 356/429 |
| 6,323,954 B1 | 11/2001 | Halter | 356/624 |
| 6,489,624 B1 | 12/2002 | Ushio | 250/559.27 |
| 6,521,905 B1 * | 2/2003 | Luxem et al. | 250/559.09 |
| 2004/0056216 A1 * | 3/2004 | Inenaga et al. | 250/548 |

FOREIGN PATENT DOCUMENTS

JP 2000-97867 4/2000

* cited by examiner

*Primary Examiner*—Thanh X. Luu
*Assistant Examiner*—Stephen Yam
(74) *Attorney, Agent, or Firm*—Sughrue Mion, PLLC

(57) ABSTRACT

Illuminating light emitted from a light source is led via a condenser lens, an optical fiber, a half-silvered mirror, and a condenser lens to a reflector. The reflector reflects the illuminating light to a CCD device through a telecentric optical system which comprises the condenser lens, the half-silvered mirror, and an aperture member. The illuminating light applied to the CCD device is greatly reduced in amount as it passes through a light-transmissive sheet-like body twice. The light-transmissive sheet-like body itself or an edge thereof can be detected with high accuracy even if the light-transmissive sheet-like body has a high transmittance.

3 Claims, 8 Drawing Sheets

APPARATUS FOR DETECTING LIGHT-TRANSMISSIVE SHEET-LIKE BODY

This is a continuation of application Ser. No. 10/060,148 filed Feb. 1, 2002 now U.S. Pat. No. 6,943,363. The entire disclosure of the prior application, application number 10/060,148 is hereby incorporated by reference.

BACKGROUND OF THE INVENTION

1. Field of the Invention

The present invention relates to an apparatus for detecting a light-transmissive sheet-like body having a high transmittance or an edge thereof highly accurately.

2. Description of the Related Art

One known apparatus for detecting minute defects in a light-transmissive substrate made of glass or the like is shown in FIG. 1 of the accompanying drawings (see Japanese laid-open patent publication No. 2000-97867). The apparatus has a light source 2 for emitting illuminating light 4 and a telecentric optical system including a condenser lens 6 and an aperture member 8 for leading the illuminating light 4 to a CCD (Charge-Coupled Device) camera 10. When a light-transmissive substrate 12 having a defect is placed between the light source 2 and the condenser lens 6, the defect in the light-transmissive substrate 12 diffuses the illuminating light 4, changing the amount of transmitted light. The illuminating light 4 which has passed through the light-transmissive substrate 12 is led through the telecentric optical system to the CCD camera 10, which produces a high-contrast image of the defect.

While the conventional apparatus is capable of effectively detecting the defect in the light-transmissive substrate 12, it is difficult for the apparatus to detect, with high accuracy, an edge 14 of the light-transmissive substrate 12 or the light-transmissive substrate 12 itself.

Specifically, if the transmittance of the light-transmissive substrate 12 is large, then any difference between shadow and highlight areas of the image of the light-transmissive substrate 12 is very small. When the light-transmissive substrate 12 vibrates while it is being detected or if the light-transmissive substrate 12 has transmittance variations, the accuracy with which to detect the light-transmissive substrate 12 is greatly reduced.

SUMMARY OF THE INVENTION

It is therefore a general object of the present invention to provide an apparatus for detecting a light-transmissive sheet-like body or an edge thereof stably with high accuracy.

An object of the present invention is to provide an apparatus for detecting a light-transmissive sheet-like body whose edge can be detected in emphasis.

Another object of the present invention is to provide an apparatus for detecting a light-transmissive sheet-like body whose edge can be detected with high accuracy without being adversely affected by positional displacements of the light-transmissive sheet-like body.

Still another object of the present invention is to provide an apparatus for detecting a light-transmissive sheet-like body whose length can be detected with high accuracy.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 2:
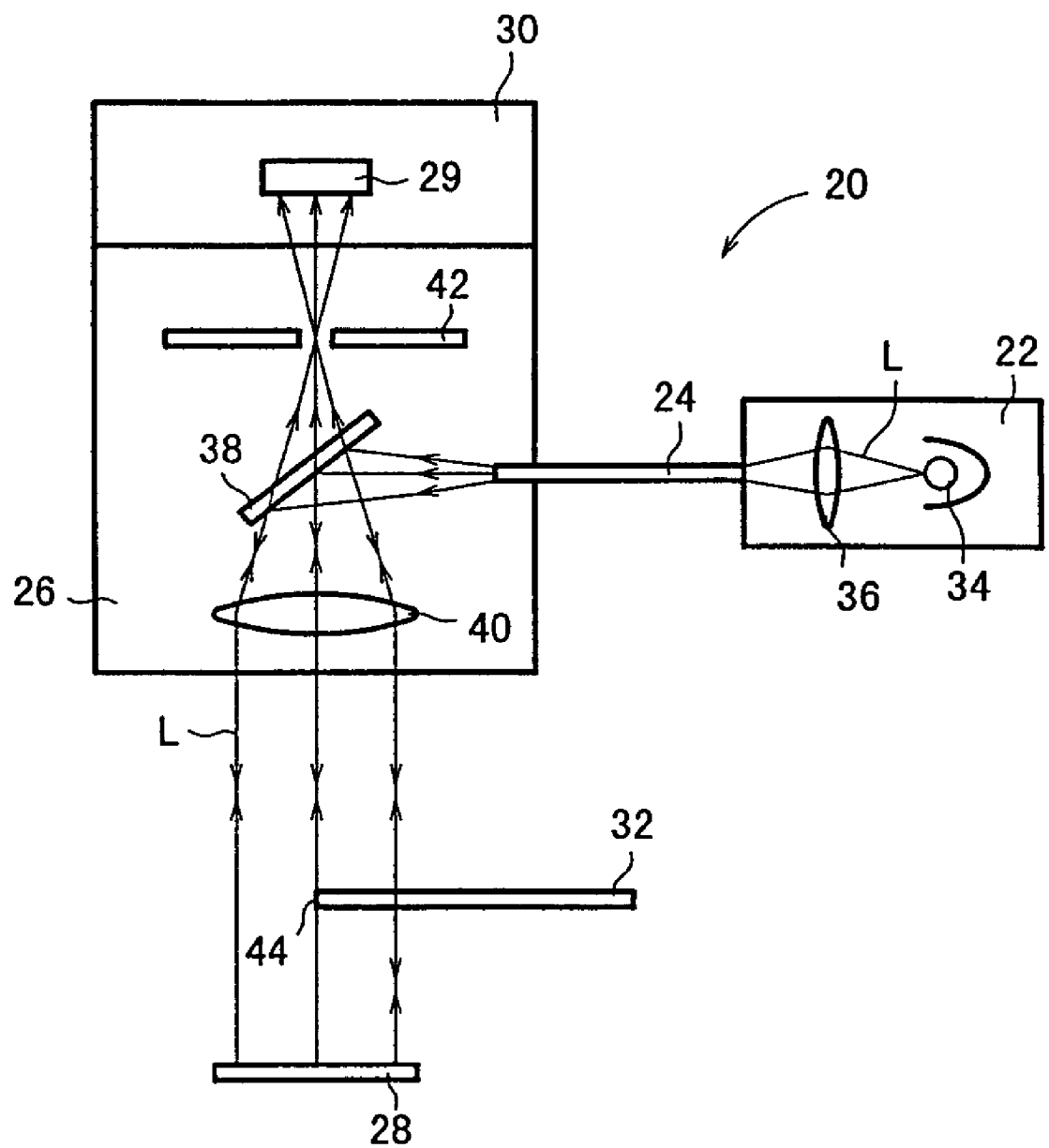
FIG. 2 is a schematic view of an apparatus for detecting a light-transmissive sheet-like body according to a first embodiment of the present invention.

FIG. 2 shows a basic arrangement of an apparatus 20 for detecting a light-transmissive sheet-like body according to a first embodiment of the present invention. As shown in FIG. 2, the apparatus 20 basically comprises a light source unit 22 for emitting illuminating light L, an optical unit 26 (converging optical system) connected to the light source unit 22 by an optical fiber 24, a reflector 28 for reflecting the illuminating light L, and a CCD camera 30 (light detecting means) for detecting the illuminating light L reflected by the reflector 28 with a CCD device 29 which serves as a two-dimensional area sensor, thereby to provide two-dimensional information on the distribution of the illuminating light L. A light-transmissive sheet-like body 32 to be detected is placed between the reflector 28 and the optical unit 26.

The light source unit 22 comprises a light source 34 for emitting the illuminating light L and a condenser lens 36 for converging the illuminating light L onto an end of the optical fiber 24.

The optical unit 26 comprises a half-silvered mirror 38 for reflecting the illuminating light L outputted from the other end of the optical fiber 24, a condenser lens 40 for converging the illuminating light L reflected by the half-silvered mirror 38 into parallel-beam light-transmissive light L and leading the parallel-beam light-transmissive light L to the reflector 28, and an aperture member 42 disposed at an image-side focal point of the condenser lens 40. The optical unit 26 comprises a telecentric optical system.

The apparatus 20 according to the first embodiment is basically constructed as described above. Operation and advantages of the apparatus 20 will be described below.

The illuminating light L emitted from the light source 34 of the light source unit 22 is converged by the condenser lens 36, and led through the optical fiber 24 to the optical unit 26. In the optical unit 26, the illuminating light L is reflected by the half-silvered mirror 38, converged by the condenser lens 40 into parallel-beam light-transmissive light L, which is led to the light-transmissive sheet-like body 32. The light-transmissive light L then passes through the light-transmissive sheet-like body 32, is reflected by the reflector 28, passes again through the light-transmissive sheet-like body 32, and reenters the optical unit 26. In the optical unit 26, the light-transmissive sheet-like body 32 travels through the half-silvered mirror 38 and the aperture member 42 and is applied to the CCD device 29 of the CCD camera 30, which detects the applied amount of illuminating light L and outputs an electric signal representing the detected amount of illuminating light L.

The illuminating light L which travels from the optical unit 26 to the reflector 28 and then back from the reflector 28 to the optical unit 26 includes light transmitted through the light-transmissive sheet-like body 32 and light bypassing the light-transmissive sheet-like body 32. Since the illuminating light L transmitted through the light-transmissive sheet-like body 32 passes through the light-transmissive sheet-like body 32 twice, the amount of the illuminating light L that falls on the CCD device 29 is greatly reduced. If any reflection by the surfaces of the light-transmissive sheet-like body 32 is ignored, then the amount of illuminating light L which falls on the CCD device 29 is reduced at a rate of the square of the transmittance of the light-transmissive sheet-like body 32. However, the illuminating light L bypassing the light-transmissive sheet-like body 32 and falling on the CCD device 29 is not reduced in amount. Therefore, it is possible to determine whether the light-transmissive sheet-like body 32 is placed between the optical unit 26 and the reflector 28 or not from the amount of illuminating light L detected by the CCD device 29.

Figure 1:
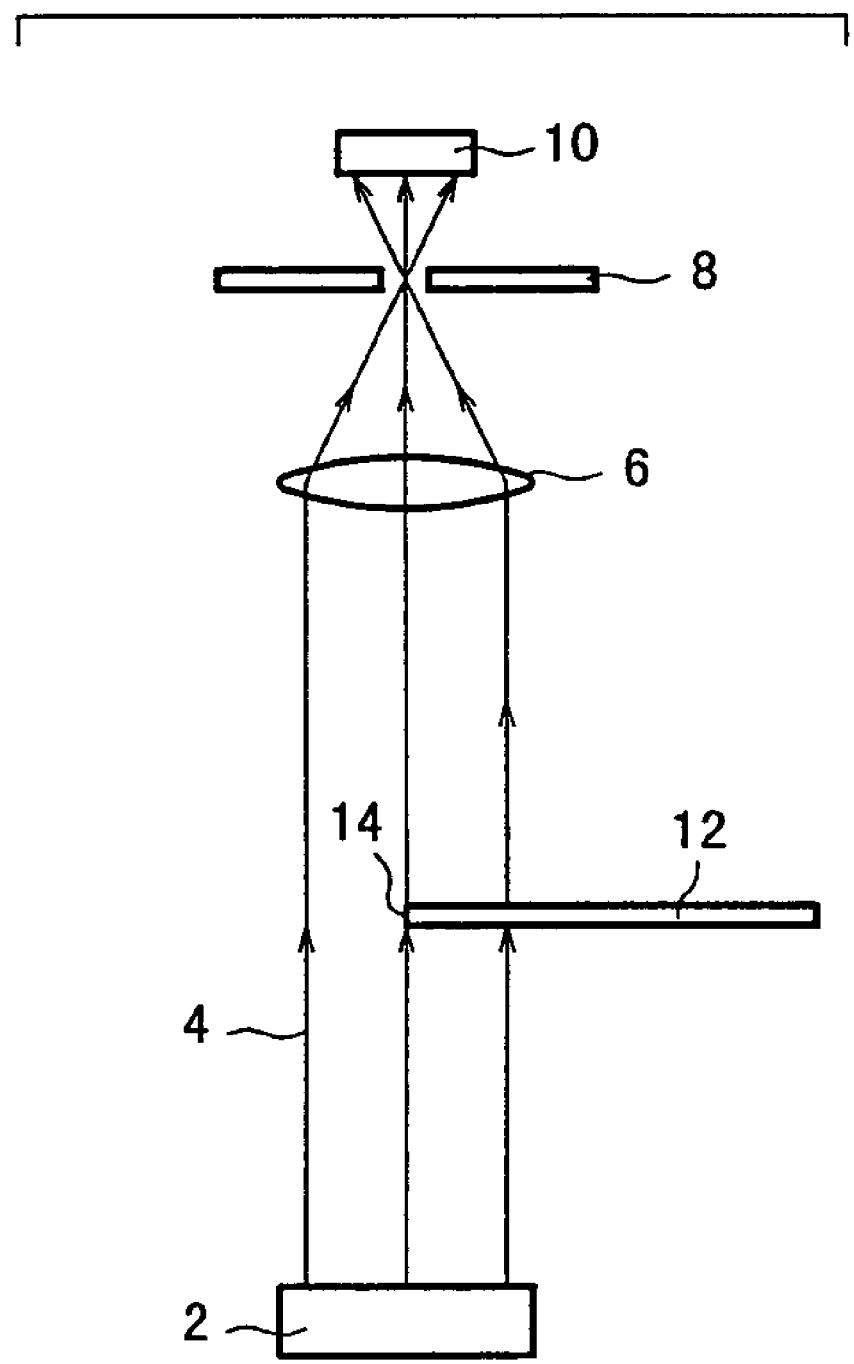
FIG. 1 is a schematic view of a conventional apparatus for detecting a defect in a light-transmissive substrate.
Figure 3:
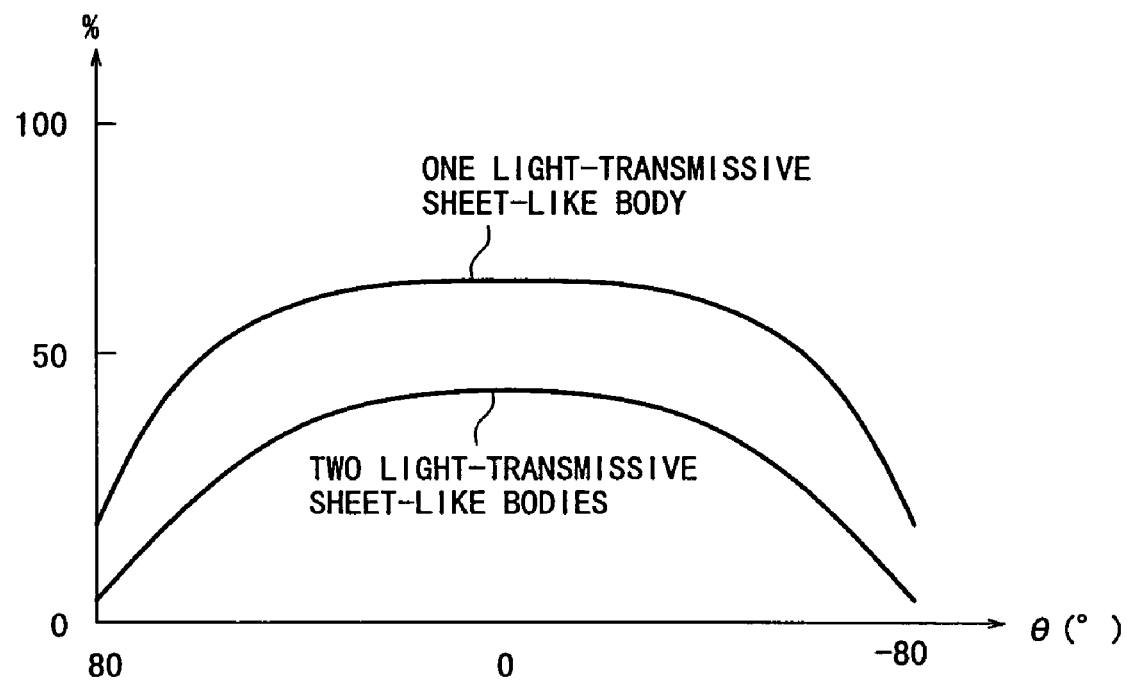
FIG. 3 is a diagram showing the relationship between the angle of incidence of illuminating light on a light-transmissive sheet-like body and the amount of light transmitted therethrough.

FIG. 3 shows, for comparison, the transmittances (%) at various incident angles θ of a single light-transmissive sheet-like body whose transmittance at an incident angle θ of 0° is 70%, and the transmittances (%) at various incident angles θ of two light-transmissive sheet-like bodies whose transmittance at an incident angle θ of 0° is 70%. It can be seen from FIG. 3 that the apparatus 20 in which the illuminating light L passes through the light-transmissive sheet-like body 32 twice is capable reducing a greater amount of illuminating light L than the conventional apparatus shown in FIG. 1 in which the illuminating light 4 passes through the light-transmissive sheet-like body 12 once. Therefore, the apparatus 20 can effectively determine whether the light-transmissive sheet-like body 32 is placed between the optical unit 26 and the reflector 28 or not.

Since the apparatus 20 according to the first embodiment employs a telecentric optical system, the amount of illuminating light L which is detected by the CCD device 29 differs greatly depending on whether the light-transmissive sheet-like body 32 is placed between the optical unit 26 and the reflector 28 or not, as shown in Table 1 below. Table 1 shows, for comparison, detected levels of illuminating light L which is applied directly to the CCD camera 20 after having passed through and bypassed the light-transmissive sheet-like body 32 whose transmittance is 70% (general optical system+transmissive illumination: optical condition 1), detected levels of illuminating light L which is applied to the CCD camera 20 via a telecentric optical system after having passed through and bypassed the light-transmissive sheet-like body 32 (telecentric optical system+transmissive illumination: optical condition 2, see FIG. 1), and detected levels of illuminating light L which is reflected by the reflector 28 and applied to the CCD camera 20 via a telecentric optical system after having passed through and bypassed the light-transmissive sheet-like body 32 (telecentric optical system+coaxial epi-illumination: optical condition 3, see the first embodiment). It is assumed in Table 1 that the output signal produced by the CCD camera 30 when a maximum amount of light falls on the CCD camera 30 has a level of 255 and the output signal produced by the CCD camera 30 when a minimum amount of light, i.e., no illuminating light L, falls on the CCD camera 30 has a level of 0.

TABLE 1

| Optical conditions | Light passing through sheet | Light bypassing sheet | Shadow – highlight difference |
|---|---|---|---|
| Optical condition 1 | 125 | 150 | 25 |
| Optical condition 2 | 114 | 156 | 42 |
| Optical condition 3 | 95 | 210 | 115 |

In the optical condition 1 (general optical system+transmissive illumination), the difference between detected signals produced when the illuminating light L passes through and bypasses the light-transmissive sheet-like body 32, i.e., the difference between shadow and highlight areas, has a level of 25. In the optical condition 2 (telecentric optical system+transmissive illumination), the difference between the detected signals has a level of 42. Accordingly, the telecentric optical system is effective in making the resultant image clear. In the optical condition 3 (telecentric optical system+coaxial epi-illumination) according to the second embodiment, the difference between the detected signals has a much higher level of 115 due to a large amount of illuminating light L which is reduced by the coaxial epi-illumination arrangement. Consequently, the arrangement based on the telecentric optical system+coaxial epi-illumination is capable of reliably detecting whether the light-transmissive sheet-like body 32 is present or not even through the light-transmissive sheet-like body 32 has a large transmittance.

Figure 4:
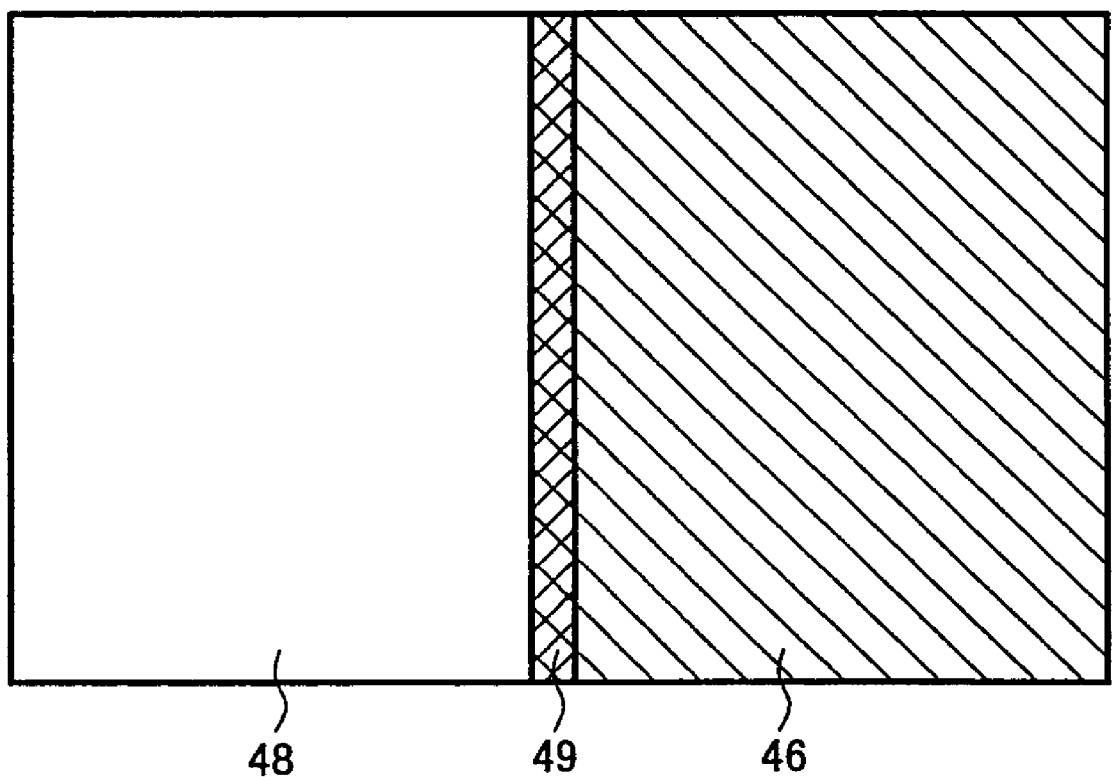
FIG. 4 is a view of an image of a light-transmissive sheet-like body which is detected by the apparatus according to the first embodiment.

The apparatus 20 according to the first embodiment is also capable of detecting an edge 44 of the light-transmissive sheet-like body 32 with high accuracy as well as the light-transmissive sheet-like body 32 itself. FIG. 4 schematically shows a two-dimensional image which is produced by the CCD device 29 when the light-transmissive sheet-like body 32 is positioned as shown in FIG. 2. The two-dimensional image includes an image 46 that is formed by the illuminating light L that has passed through the light-transmissive sheet-like body 32 twice, an image 48 that is formed by the illuminating light L that has bypassed the light-transmissive sheet-like body 32 and been reflected by the reflector 28, and an image 49 that is formed by the edge 44 of the light-transmissive sheet-like body 32.

Since the edge 44 refracts and diffuses the illuminating light L, the edge 44 is greatly effective to reduce the amount of illuminating light L passing therethrough. Since the optical unit 26 comprises a telecentric optical system, the illuminating light L applied to the CCD device 29 is limited to principal light rays. Therefore, the image 49 representing the edge 44 is lower in intensity than the image 46, allowing the edge 44 to be detected with high accuracy.

Figure 5:
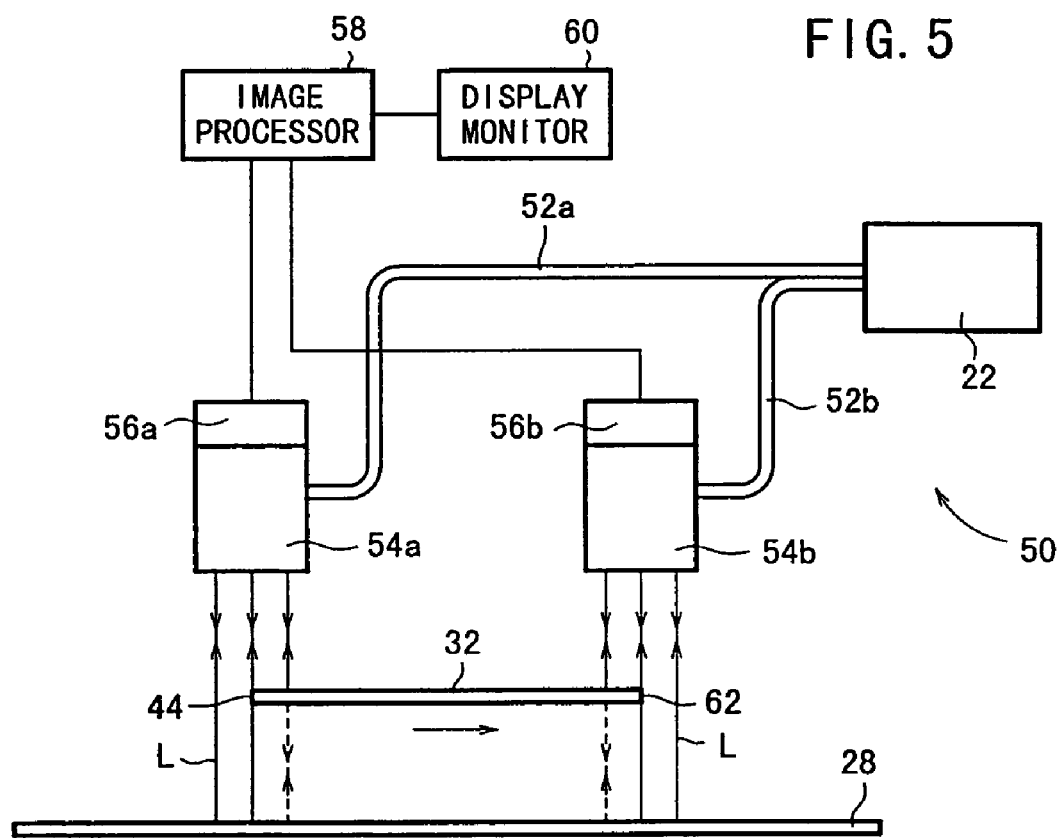
FIG. 5 is a schematic view of an apparatus for detecting a light-transmissive sheet-like body according to a second embodiment of the present invention.

FIG. 5 schematically shows an apparatus 50 for detecting a light-transmissive sheet-like body according to a second embodiment of the present invention. Those parts of the apparatus 50 which are identical to those of the apparatus 20 shown in FIG. 2 are denoted by identical reference characters, and will not be described in detail below.

As shown in FIG. 5, the apparatus 50 comprises a light source unit 22 for emitting illuminating light L, a pair of optical units 54a, 54b (converging optical systems) for leading the illuminating light L from the light source unit 22 to a reflector 28 via respective optical fibers 52a, 52b, a pair of CCD cameras 56a, 56b (light detecting means) for detecting the illuminating light L reflected by the reflector 28 via the respective optical units 54a, 54b, an image processor 58 (processing means) for processing images captured by the CCD cameras 56a, 56b, and a display monitor 60 for displaying the images processed by the image processor 58.

The apparatus 50 thus constructed is capable of measuring, with high accuracy, the length of a light-transmissive sheet-like body 32 which is placed between the reflector 28 and the optical units 54a, 54b and fed in the direction indicated by the arrow.

Figure 6:
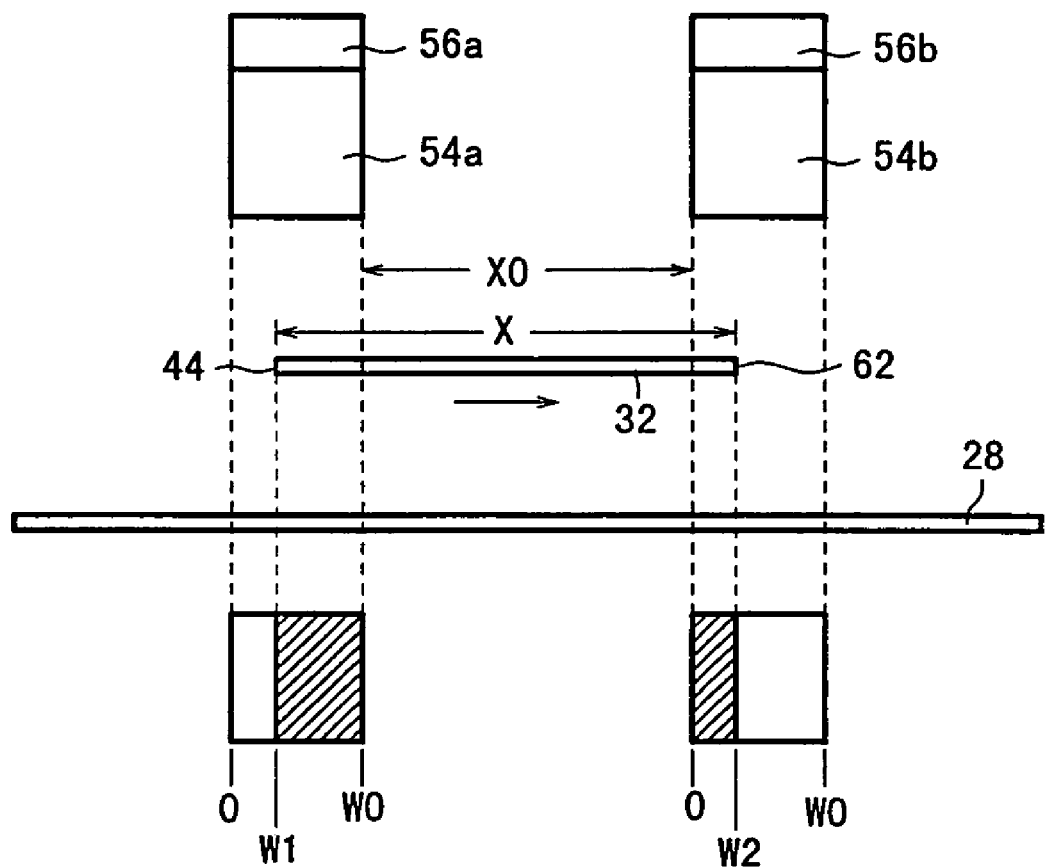
FIG. 6 is a schematic view illustrating the manner in which the length of a light-transmissive sheet-like body is determined by the apparatus according to the second embodiment.
Figure 7:
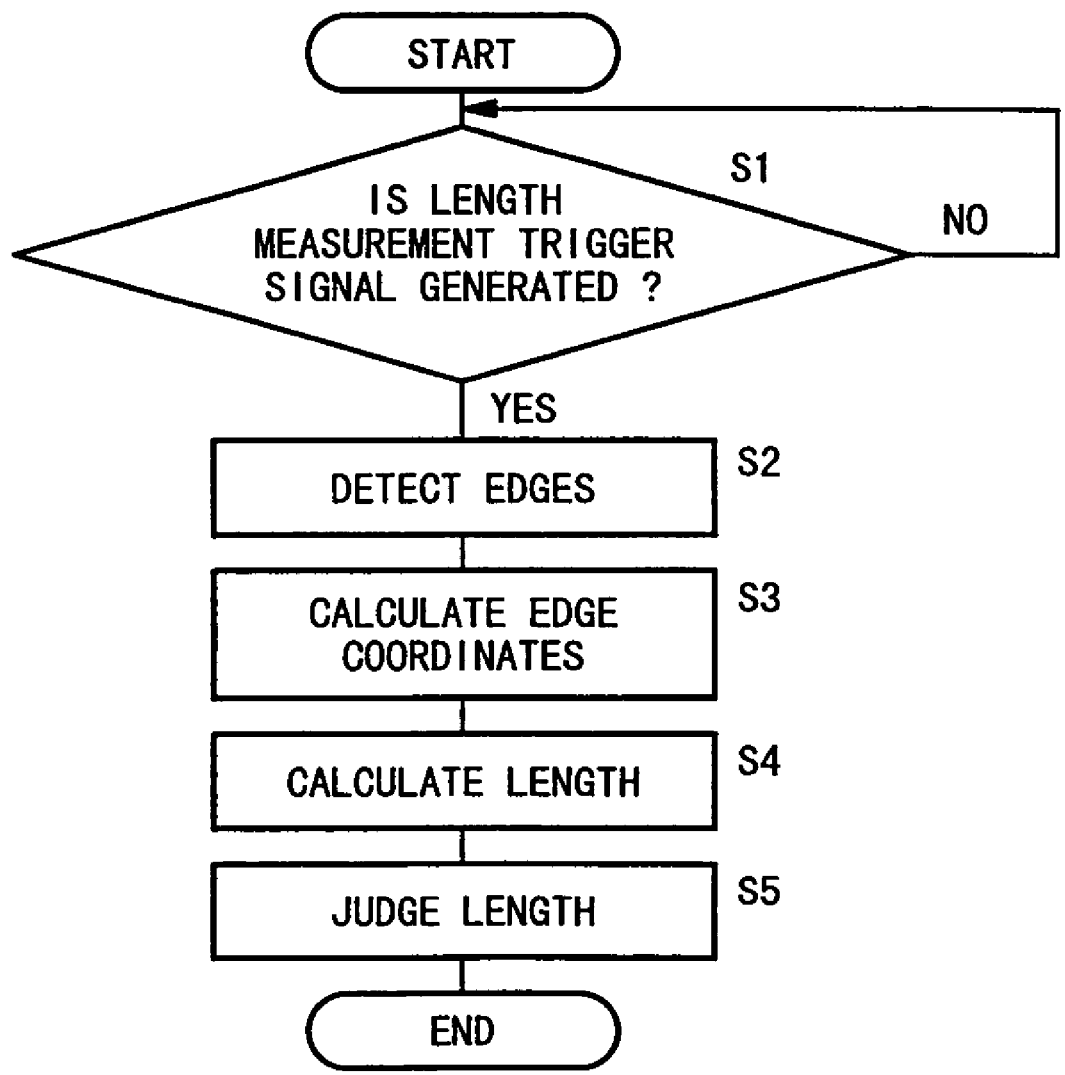
FIG. 7 is a flowchart of a process of calculating the length of a light-transmissive sheet-like body with the apparatus according to the second embodiment.

The CCD cameras 56a, 56b capture respective images of an edge 44 of the light-transmissive sheet-like body 32 and an opposite edge 62 thereof, and supply the captured images to the image processor 58. The image processor 58 displays the captured images on the display monitor 60. The image processor 58 also calculates the positions of the edges 44, 62 from the images, and determines the length of the light-transmissive sheet-like body 32 from the calculated positions of the edges 44, 62. A process of determining the length of the light-transmissive sheet-like body 32 will be described below with reference to FIGS. 6 and 7.

First, the light-transmissive sheet-like body 32 is introduced into a predetermined length measurement range. If a length measurement trigger signal is generated in step S1 shown in FIG. 7, then the image processor 58 starts a process of detecting the edges 44, 62 of the light-transmissive sheet-like body 32 in step S2. Specifically, the image processor 58 scans the images captured by the CCD cameras 56a, 56b in the direction in which the light-transmissive sheet-like body 32 is fed, and detects areas where the image density changes a predetermined quantity as the edges 44, 62.

Thereafter, the image processor 58 calculates the coordinates of the edges 44, 62 in step S3. The coordinates are calculated by setting the coordinates of the upstream ends of the CCD cameras 56a, 56b to "0" and determining coordinates from the coordinates "0" up to pixels where the edges 44, 62 are detected, as coordinates W1, W2 of the edges 44, 62.

Using the coordinates W1, W2 of the edges 44, 62 thus determined, the image processor 58 calculates the length X of the light-transmissive sheet-like body 32 in step S4. Specifically, if the distance between the images captured respectively by the cameras 56a, 56b is indicated by X0 and the coordinates of the downstream ends of the images are indicated by W0, then the length X of the light-transmissive sheet-like body 32 is determined as follows:

$$X = W0 - W1 + W2 + X0$$

If the values W0, W1, W2, X0 represent the numbers of pixels, then the value X is multiplied by the size of each pixel to determine the length X.

After the length X of the light-transmissive sheet-like body 32 is determined, the image processor 58 determines whether the length X is acceptable or not in step S5. Thereafter, the process is put to an end.

Since each of the optical units 54a, 54b comprises a telecentric optical system which is telecentric on the object side, even if the position of the light-transmissive sheet-like body 32 varies in the direction of the optical axis of the telecentric optical system, the position of the edge 44 can be detected highly accurately without being adversely affected by the positional variation. Therefore, the length X of the light-transmissive sheet-like body 32 can also be detected highly accurately.

Figure 8:
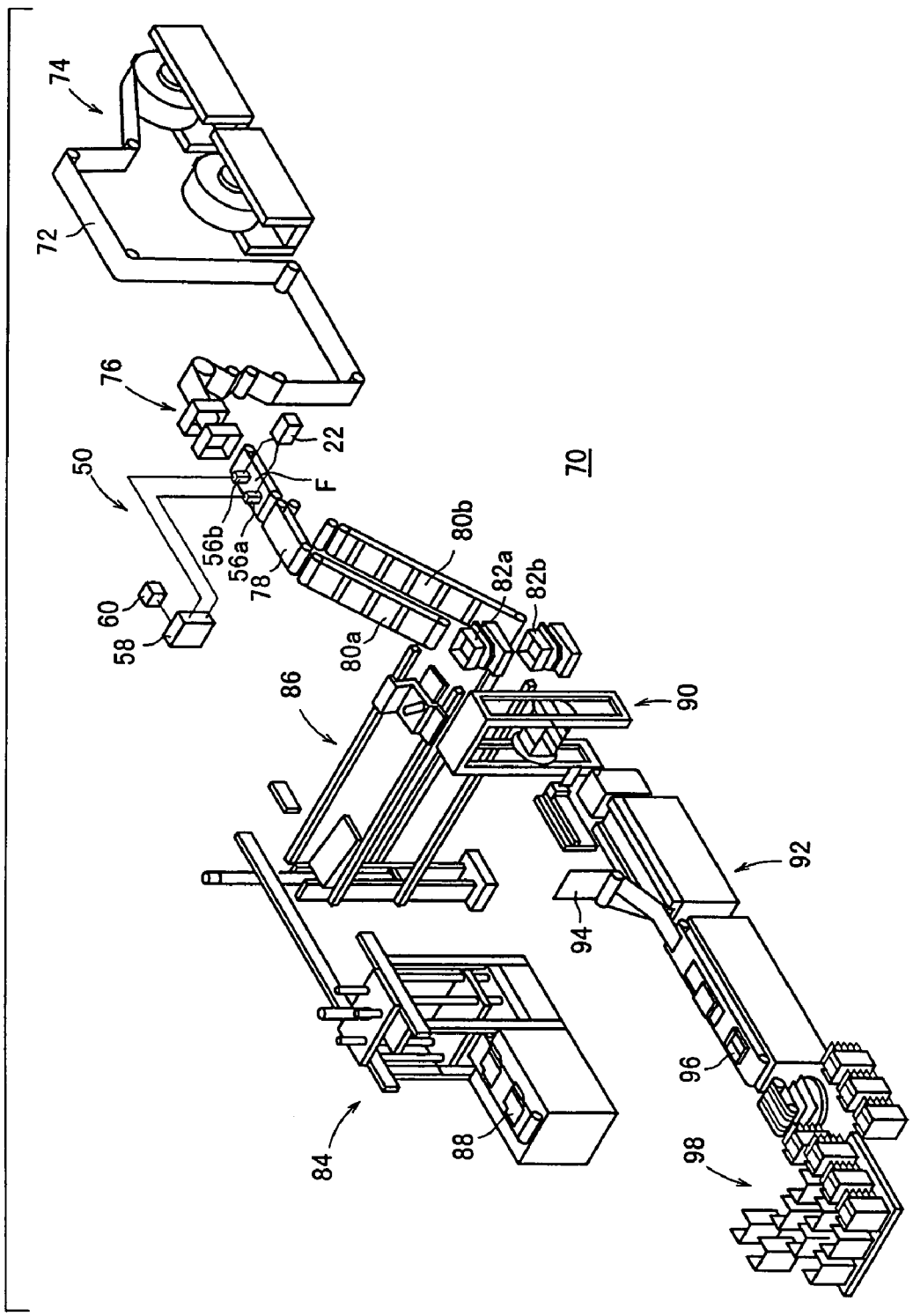
FIG. 8 is a schematic perspective view of a film production system which incorporates the apparatus according to the second embodiment.

FIG. 8 shows in perspective a film production system 70 which incorporates the apparatus 50 shown in FIG. 5.

In the film production system 70, a roll film 72 of a rolled photosensitive material is unwound and supplied from a film supply unit 74, and cut into a succession of films F of given length by a film cutting unit 76. The cut films F are then fed along a film feed line 78, sorted to an upper feed line 80a and a lower feed line 80b, and then supplied to film stack producing devices 82a, 82b.

In each of the film stack producing devices 82a, 82b, films F are stacked on a protective cover 88 which is supplied from a protective cover supply device 84 through a protective cover feed mechanism 86. The produced stack of films F is supplied to a stack reversing device 90 in which the stack is vertically reversed, i.e., turned upside down. The stack of films F is then placed in a light-shielding package 94 in a packaged product manufacturing device 92, thus producing a packaged product 96. Packaged products 96 thus manufactured are stacked in a packaged product stacking device 98, and then shipped from the film production system 70.

In the film production system 70 thus constructed, the apparatus 50 is disposed on the film feed line 78. The film feed line 78 functions as the reflector 28. The illuminating light L emitted from the light source unit 22 has a wavelength of 850 nm or higher because the films F are of a photosensitive material sensitive to visible light.

The length of each of the films F supplied to the film feed line 78 is determined by the apparatus 50. If the determined length is not acceptable, then the film F is rejected as a defective film from the film feed line 78. Based on the determined length, the film F may be sorted and supplied to the upper feed line 80a or the lower feed line 80b.

Although certain preferred embodiments of the present invention have been shown and described in detail, it should be understood that various changes and modifications may be made therein without departing from the scope of the appended claims.

What is claimed is:

1. An apparatus for detecting a light-transmissive sheet-like body, comprising:

a light source unit for emitting illuminating light;

light detecting means for detecting the illuminating light; and an optical system for leading the illuminating light as parallel-beam light to the light-transmissive sheet-like body and converging the illuminating light to said light detecting means, wherein an edge of the light-transmissive sheet-like body placed between said light source unit and said optical system is detected based on a difference between two types of information, said two types of information including information of said illuminating light which is led to said light detecting means through said edge and another information of said illuminating light which bypasses said edge and is led to said light detecting means, and wherein said illuminating light passes twice through said light-transmissive sheet-like body.

2. The apparatus of claim 1, wherein said light detecting means is oriented lengthwise parallel to a direction of travel of the light-transmissive body, to receive light which bypasses the edge and to receive light which passes through said edge.

3. The apparatus of claim 2, wherein said light detecting means detects light which bypasses said edge and which passes through said edge, said edge comprising a leading edge of the light-transmissive body.

* * * * *